US012766114B2

(12) United States Patent
Ham

(10) Patent No.: US 12,766,114 B2
(45) Date of Patent: Oct. 20, 2026

(54) MATRIX TYPE HYDROGEL PATCH FOR TOENAIL CARE

(71) Applicants: Yun Beom Ham, Ansan-si (KR); Chinna Chinnakaruppan, Bridgewater, NJ (US)

(72) Inventor: Yun Beom Ham, Ansan-si (KR)

(73) Assignees: Yun Beom Ham, Ansan-si (KR); Chinna Chinnakaruppan, Bridgewater, NJ (US)

( * ) Notice: Subject to any disclaimer, the term of this patent is extended or adjusted under 35 U.S.C. 154(b) by 162 days.

(21) Appl. No.: 18/991,659

(22) Filed: Dec. 22, 2024

(65) Prior Publication Data

US 2026/0174709 A1 Jun. 25, 2026

(51) Int. Cl.

| | |
|---|---|
| ***A61K 31/12*** | (2006.01) |
| ***A61K 8/02*** | (2006.01) |
| ***A61K 8/34*** | (2006.01) |
| ***A61K 8/35*** | (2006.01) |
| ***A61K 8/365*** | (2006.01) |
| ***A61K 8/42*** | (2006.01) |
| ***A61K 8/81*** | (2006.01) |
| ***A61K 9/70*** | (2006.01) |
| ***A61K 31/17*** | (2006.01) |
| ***A61K 47/10*** | (2017.01) |

(Continued)

(52) U.S. Cl.
CPC ............ *A61K 31/12* (2013.01); *A61K 8/0233* (2013.01); *A61K 8/345* (2013.01); *A61K 8/35* (2013.01); *A61K 8/365* (2013.01); *A61K 8/42* (2013.01); *A61K 8/8147* (2013.01); *A61K 9/7007* (2013.01); *A61K 31/17* (2013.01); *A61K 47/10* (2013.01); *A61K 47/12* (2013.01); *A61K 47/32* (2013.01); *A61P 17/00* (2018.01); *A61Q 3/00* (2013.01)

(58) Field of Classification Search
CPC ...... A61K 31/12; A61K 8/0233; A61K 8/345; A61K 8/35; A61K 8/365; A61K 8/42; A61K 8/8147; A61K 9/7007; A61K 31/17; A61K 47/10; A61K 47/12; A61K 47/32; A61K 8/36; A61P 17/00; A61Q 3/00
See application file for complete search history.

(56) References Cited

U.S. PATENT DOCUMENTS 7,588,753 B2 * 9/2009 Ferrandis ................ A61P 31/04 424/404
8,987,330 B2 * 3/2015 Karlsson .............. A61K 31/197 514/557
9,782,372 B2 * 10/2017 Karlsson ................ A61K 47/10

FOREIGN PATENT DOCUMENTS

KR 10-2005-0042488 A 5/2005
KR 10-1582448 B1 1/2016

OTHER PUBLICATIONS

Taurinya, Guillem; Thèse pour le diplôme d'État de docteur en Pharmacie; "Les mycoses du pied: différents types, diagnostic, traitements et conseils à l'officine."; presented and publicly defended on Sep. 14, 2020.*

* cited by examiner

*Primary Examiner* — Jeffrey T. Palenik
(74) *Attorney, Agent, or Firm* — Revolution IP, PLLC

(57) ABSTRACT

The present invention relates to a hydrogel patch for nail care, wherein the composition of the hydrogel patch according to the present invention is characterized by combination of the main ingredients of hydroxyethyl urea and resacetophenone and is superior to previous products in terms of the cuticle, surface roughness, surface gloss, moisture content, blood circulation, and nail appearance improvement effects, and also improves the convenience of use.

5 Claims, 6 Drawing Sheets

(51) Int. Cl.

| | |
|---|---|
| ***A61K 47/12*** | (2006.01) |
| ***A61K 47/32*** | (2006.01) |
| ***A61P 17/00*** | (2006.01) |
| ***A61Q 3/00*** | (2006.01) |

| No. | Before using product | After using product |
| --- | --- | --- |
| Subject 3 |  |  |
| |  |  |

| No. | Before using product | After using product |
|---|---|---|
| Subject 1 |  |  |
| Subject 2 |  |  |

| No. | Before using product | After using product one day |
|---|---|---|
| Subject 4 |  |  |
| Subject 1 |  |  |

MATRIX TYPE HYDROGEL PATCH FOR TOENAIL CARE

BACKGROUND OF THE INVENTION

The present invention relates to a toenail care composition and a method of preparing the same, and more specifically, to a multi-functional toenail care composition that simultaneously provides an appearance-improving effect and a moisture-supplying function.

[the Need for Toenail Care]

The present invention relates to a toenail care composition, and more specifically, to a multi-functional toenail care composition that simultaneously provides an appearance-improving effect and a moisture-supplying function.

The toenail is an important part of the human body that protects the tips of the toes from the external environment and absorbs shock when walking. However, the toenail may be relatively easily damaged or infected with diseases due to physical stimulation and external impact in daily living. In particular, with the change in the lifestyle of modern people, toenail-related problems are increasing, so the need for proper toenail care is emerging.

The main purpose of toenail care may be divided into two major purposes. The first is the cosmetic improvement of the toenail. Discoloration of the toenail due to aging or external factors causes aesthetic problems, and an appearance-improving effect is required to improve solve the problems. The second is the maintenance of the health of the toenail. Dryness of the toenail causes cracking or breaking, so proper moisture supply is essential.

[Limitations of Existing Technology]

Currently, toenail care products on the market mainly use urea, fumaric acid, and butylene glycol as active ingredients. These ingredients contribute to the removal of dead skin cells and moisturizing effects to some extent, but they show limitations in terms of appearance-improving effects. In addition, existing products focus on the treatment of the toenail surface, and thus has limitations in the delivery of the active ingredients to the inside of the toenail.

RELATED ART DOCUMENTS

Korean Patent Registration No. 10-1582448

Korean Patent Publication No. 10-2005-0042488

SUMMARY OF THE INVENTION

The present invention aims to overcome the limitations of existing toenail care products and solve the problems described below.

1. Toenail Cuticle-Removing and Appearance-Improving Effects

The present invention is a unique hydrogel composition containing hydroxyethyl urea and resacetophenone ingredients and aims to simultaneously provide toenail cuticle-removing and appearance-improving effects.

2. Improvement of Absorption Rate and pH Stability of Main Ingredients

Due to the nature of toenail, penetration of the main ingredients has been difficult, and thus the therapeutic effect has been limited. The present invention aims to increase the absorption rate of the main ingredients by increasing the permeability of the toenail surface through three x-hydroxy-acid (AHA) ingredients (lactic acid, glycolic acid, tartaric acid). In addition, the goal is to develop a formulation with a stable pH despite the use of these acidic substances.

3. Realization of Long-Lasting Moisturizing Effect

Existing urea-based products provide temporary moisturizing effect but lack sustainability. The present invention aims to achieve a strong moisturizing effect lasting up to 12 hours by using hydroxyethyl urea (50%).

4. Minimization of Skin Irritation

Existing dead cell-dissolving products containing AHA ingredients often cause skin irritation. The present invention aims to minimize skin irritation while maintaining effective toenail care action, by developing a hydrogel composition containing various effective ingredients.

5. Securing Productivity and Quality

Due to the characteristics of hydrogel manufacturing, appropriate gel strength is an important factor that is directly related to the application process and determines both production and quality. The goal is to develop a product with stable productivity and excellent quality by studying the prescription of appropriate gel strength.

6. Antibacterial Effect of Hydrogel

The goal is to secure the stability of hydrogel in the product against bacteria by excluding parabens, which are commonly used in existing hydrogel patches, and using 1,2-hexanediol instead.

By solving these problems, the present invention aims to overcome the limitations of existing products and provide a more effective and safe toenail care solution. The present invention is expected to contribute to improving the toenail health and quality of life of users.

The present invention has solved the above-described problems by the means described below.

1. A hydrogel composition for a nail care patch, including hydroxyethyl urea and resacetophenone, wherein the hydrogel composition includes sodium polyacrylate as a gel-forming hydrophilic polymer, and the hydroxyethyl urea is preferably hydroxyethyl urea (50%).

2. The hydrogel composition according to the above item 1, wherein the hydroxyethyl urea is included in an amount of 10% to 20% by weight based on the total composition, and the resacetophenone is included in an amount of 0.3% to 0.7% by weight based on the total composition.

3. The hydrogel composition according to the above item 1 or item 2, further including lactic acid, glycolic acid, and tartaric acid as nail permeability enhancers of hydroxyethyl urea and resacetophenone, wherein the three ingredients, lactic acid, glycolic acid, and tartaric acid, are included in a total amount of at least 2% by weight based on the total composition.

4. The hydrogel composition according to any one of the above item 1 to item 3, further including 1,2-hexanediol without containing preservative parabens, wherein bacterial do not grow during the shelf life of product.

5. The hydrogel composition according to any one of the above item 1 to item 4, further including glycerin, water, tocopheryl acetate, 1,2-hexanediol, sodium polyacrylate, carmellose sodium, aluminum glycinate, disodium edetate, or 1,3-butylene glycol in an amount of 25% to 35% by weight, 35% to 45% by weight, 0.2% to 0.4% by weight, 4% to 6% by weight, 2% to 4% by weight, 0.07% to 0.14% by weight, 0.06% to 0.12% by weight, 5% to 10% by weight, respectively, based on the total composition.

6. The hydrogel composition according to any one of the above item 1 to item 5, wherein the pH of the composition is within the range from 4.5 to 5.5.

7. The hydrogel composition according to any one of the above item 1 to item 6, wherein the gel strength of the composition is 150 gf to 450 gf, application work may be performed in one hour when manufacturing a hydrogel patch, and the compressive strength is measured at room temperature as the gel strength.

8. The hydrogel composition according to any one of the above item 1 to item 7, wherein the hydrogel composition is effective for improving cuticles, improving nail surface roughness, or improving hemoglobin concentration in skin around nails (blood circulation).

9. A hydrogel patch manufactured by applying the hydrogel composition according to any one of the above item 1 to item 8 on a nonwoven fabric.

10. The hydrogel patch according to the above item 9, wherein the formulation includes a triple structure of a urethane-coated nonwoven fabric (thickness 1 to 2 mm), a matrix hydrogel (thickness 0.5 to 1.5 mm), and a cross-section silicone-treated embossed polyethylene terephthalate (PET) film release paper, as shown in FIG. 1.

11. The hydrogel patch according to the above item 9, wherein the formulation is a band type including a triple structure of an apricot-colored nonwoven fabric, a hydrogel patch composition, and a double-overlapping PET film, as shown in FIG. 2.

12. The hydrogel patch according to any one of the above item 9 to item 11, wherein, after being attached to a nail, the hydrogel patch remains stable for 8 to 12 hours and the main ingredient is gradually released.

The present invention is a novel hydrogel patch for toenail care that simultaneously provides toenail antifungal effects and appearance-improving effects. The main features of the present invention are described below.

1. Resacetophenone: A key main ingredient that provides an appearance-improving effect and exhibits excellent efficacy in removing cuticles.

2. Hydroxyethyl urea (50%): A high-concentration moisture-supplying main ingredient that greatly improves the moisturizing power of toenail and surrounding skin and has excellent efficacy in removing cuticles.

3. Three AHA ingredients (lactic acid, glycolic acid, tartaric acid): Ingredients increasing the permeability of the toenail surface and removing dead cells, thereby increasing the absorption rate of the main ingredients.

4. Hydrogel patch form: Patch form enabling continuous and effective delivery of the main ingredients and increasing convenience of use. In addition, it maximizes the toenail care effect through sufficient moisture supply and moisturizing power. The goal is to secure the stability of the hydrogel in the product against bacteria by excluding parabens, which are commonly used in existing hydrogel patches, and using 1,2-hexanediol instead. By studying a prescription with appropriate gel strength, the present invention contributes to improving the productivity and quality of the product.

Compared to existing products, the present invention provides the advantages described below.

1. Improved stability and efficacy sustainability: Hydroxyethyl urea has superior chemical stability to urea, which is generally used in other toenail products. This improves the sustainability of the product's effects. It also improves compatibility with other ingredients, thereby increasing the stability of the formulation. Furthermore, hydroxyethyl urea has significantly lower skin irritation than urea. This is because the skin compatibility has been improved due to the hydroxyl group ($—CH_2CH_2OH$) added to the molecular structure of hydroxyethyl urea. This allows the present invention to be safely used on sensitive skin.

2. Excellent appearance-improving effect: The synergistic effect of resacetophenone and AHA ingredients is excellent for improving toenail discoloration. In particular, through the AHA ingredients, the permeability of the toenail surface is increased, thereby promoting the absorption of the main ingredients.

3. Improved moisturizing effect: Hydroxyethyl urea has higher hydrophilicity than urea, so it has excellent moisture binding ability. The added hydroxyl group forms hydrogen bonds to increase moisture retention. This effectively prevents skin dryness that may occur during the dead cell-dissolving process and provides a long-lasting moisturizing effect. Furthermore, due to the nature of the hydrogel, approximately 40% of water and 30% of glycerin are present in the formulation, providing excellent moisture-supplying and moisturizing effects.

4. Securing productivity and quality: The development of the hydrogel prescription aims to secure productivity and product quality. Due to the nature of the hydrogel, gel strength is an important measure that determines the productivity of the product, especially the workability during the hydrogel application time, and is directly related to the product quality. The prescription of the developed formulation has secured productivity, represented by the application time within one hour, as well as high product quality, and the use of 1,2-hexanediol prevents bacterial growth in the formulation while being harmless to the human body, thereby adding to the stability of the product.

DETAILED DESCRIPTION OF THE EMBODIMENTS

[Nail Disorder]

Figure 1:
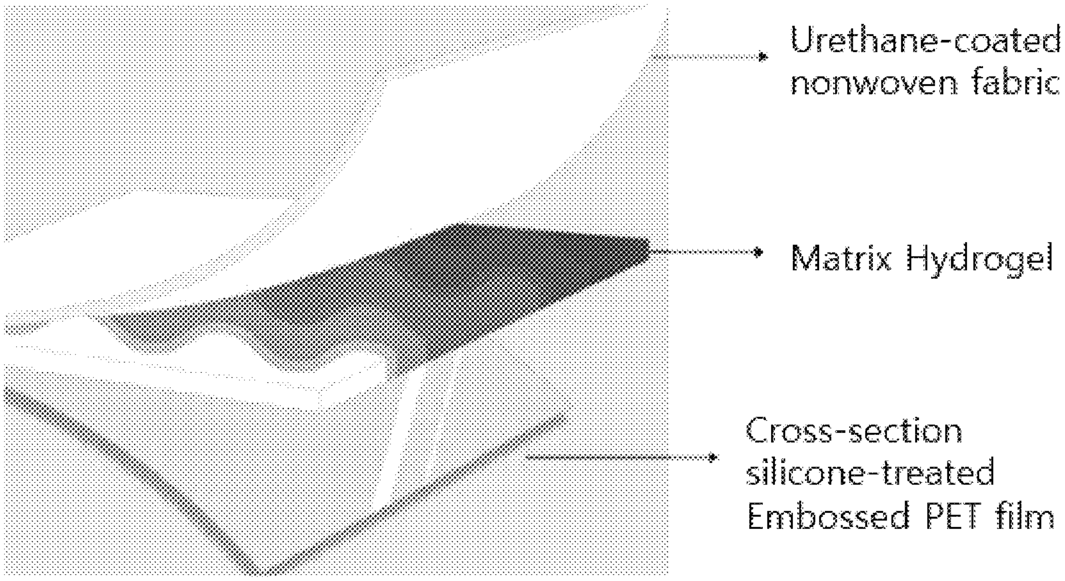
FIGS. 1 and 2 show diagrams illustrating patches according to one embodiment of the present invention.

Toenail is a type of skin that evolved from a part of the skin. Toenail is a modified dead cell layer of the skin and is made of a hard component called keratin that creates dead cells. Keratin, the main component of toenail, is harder than the keratin in the skin or hair, and is made of a hard layer consisting of, not a single epidermis, but overlapping thin layers of 0.1 to 0.2 mm. Toenail grows about 0.14 to 0.4 mm per day, and it takes about five to six months for toenail to grow completely and be replaced.

A healthy toenail should be firm and elastic, and the shape of the toenail should be properly extended. In addition, it should also be pink, form a round arch, have a smooth gloss, and contain an adequate amount of moisture.

When toenail management is insufficient, damage occurs. Damage to the toenail may be found in various ways, such as symptoms of toenails being thin and tearing down, or symptoms of toenails being dry and peeling off in layers.

A study on toenail damage and recovery showed that nail hardeners containing moisturizing ingredients and protein ingredients may be effective. An example of a nail hardener is the Envy Original product, which contains ethyl acetate, butyl acetate, nitrocellulose, and propyl acetate.

In addition, when a nail guard containing chitosan, collagen, silica gel, and oat beta-glucan was applied for 30 days and its nail protection effect was examined, the effect was similar to that of the nail hardener, although there was a difference in performance.

[Conventional Toenail Nutritional Supplements]

Korean Patent Publication No. 10-1582448 discloses a composition prepared by dissolving urea in propylene glycol and glycerol and then adding lactic acid and then NaOH. This is the basic composition of a toenail nutrition for skin application. Lactic acid is an x-hydroxyacid (AHA) ingredient that removes dead cells, propylene glycol is an ingredient that promotes nail penetration, and urea is a disinfectant or bleaching ingredient. In addition, glycerol is an ingredient added to ensure the chemical stability of urea.

However, since the above conventional toenail nutritional supplement is a formulation for skin application, there is the inconvenience that the user has to be careful for a certain period of time so that the applied medicine is not washed off until the main ingredients penetrate into the nail after applying it to the toenail. To improve this inconvenience, there are some products that further contain a water-insoluble viscous coating polymer such as ethyl cellulose, but they have the inconvenience in removing the coating formed after applying the drug solution.

On the other hand, unlike Korean Patent Publication No. 10-1582448, there are toenail nutritional supplements that contain urea solution as a main ingredient, not urea. For example, discloses a Korean Patent Publication NO. 10-2005-0042488 composition containing ethanol, ethyl acetate, butyl acetate, urea, lactic acid, a pharmaceutically active ingredient, and a film-forming polymer.

However, the conventional toenail nutritional supplements are also in the form of a formulation for skin application, so they are not convenient to use.

The above is a representative explanation about toenail, but the same applies to finger nails.

[Hydrogel Patch]

The present inventor developed a hydrogel patch formulation in order to overcome the convenience limitations of the formulation for skin application. Unlike the formulation for skin application, the present invention can be used simply by attaching a nonwoven fabric with a drug solution applied to the finger nail or toenail area, and then removing the nonwoven fabric when the drug solution is sufficiently absorbed. The use process is very simple. In addition, according to the present invention, unlike the formulation for skin application, it is possible to use it in daily living, and it can even be used while sleeping.

A hydrogel is manufactured from a hydrophilic polymer that forms a three-dimensional network structure containing a large amount of moisture, and basically requires water, polyhydric alcohol, a crosslinking agent, and a hydrophilic polymer. At this time, the hydrophilic polymer has different suitable components depending on the main ingredients contained, and in the case of the present invention, sodium polyacrylate provides appropriate gel strength and is most preferable in terms of film forming ability after hydrogel formation.

The preferred gel strength in the present invention is 150 gf to 450 gf.

[Main Ingredients]

The present invention is characterized that hydroxyethyl urea and resacetophenone are used as representative main ingredients. One embodiment of the present invention may include hydroxyethyl urea in an amount of 10% to 20% by weight based on the total composition, and may include resacetophenone in an amount of 0.3% to 0.7% by weight based on the total composition.

Urea is a molecule having a structure represented by Chemical Formula 1 below, and hydroxyethyl urea is a molecule having a structure represented by Chemical Formula 2.

[Chemical Formula 1]

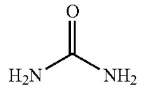

[Chemical Formula 2]

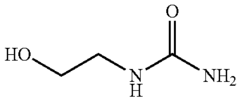

Hydroxyethyl urea is an ingredient that may be obtained by neutralizing, refining, and drying ethylene hydrolyzed in urea. Hydroxyethyl urea has the advantage that it is a more stabilized ingredient than urea, but has the disadvantage that the content has to be increased compared to urea when added for the purpose of gaining a moisturizing effect, so it is an ingredient that has not been commonly used. In particular, in the case of hydrogel patches, after a hydrogel is manufactured, it must have appropriate gel strength and be formed into a film before in order to be applied on a nonwoven fabric, but when the content of the main ingredients is large, there is a difficulty in film formation. Therefore, the adoption of hydroxyethyl urea in hydrogel patch formulations has been avoided even more.

Nevertheless, the present inventor has adopted hydroxyethyl urea as a main ingredient of the present formulation because it has an excellent appearance-improving effect as well as a dead cell-removing effect when combined with resacetophenone. Specifically, the combination of hydroxyethyl urea and resacetophenone is effective in improving cuticles, improving toenail surface roughness, or improving hemoglobin concentration around the toenail skin (blood circulation).

The present inventor experienced many failures in the process of manufacturing a hydrogel including the above-described composite main ingredients and forming a film to coat a nonwoven fabric, but it was confirmed that when sodium polyacrylate was adopted as a gel-forming polymer, a synergistic effect with the above composite main ingredients was exhibited, so that an appropriate gel strength was achieved and the hydrogel film was stably formed, thereby completing the present invention.

The gel composition of the present invention has a gel strength of 150 gf to 450 gf, and may be applied within one hour when manufacturing a hydrogel patch. In addition, the temperature of the hydrogel that is finally produced is in the range of 30 to 40° C., the pH is 4.5 to 5.5, the viscosity is 100,000 to 2,00,000 at 25° C., and the crosslinking speed is suitable for application within 90 minutes.

[Other Main Ingredients]

The present invention may further include AHA ingredients as main ingredients. AHA ingredients are known as ingredients that dissolve glue between dead cell layers and gently remove thick dead cells. Therefore, they are ingredients that have been widely used in toenail nutritional supplements for the purpose of removing dead cells.

However, the present inventor confirmed that when three specific AHA ingredients among the AHA ingredients are combined, not only can a simple dead cell-removing effect be obtained, but the absorption rate of the main ingredients can also increase by additionally increasing the toenail surface permeability of hydroxyethyl urea and resacetophenone.

The three preferred AHA ingredients in the present invention are lactic acid, glycolic acid, and tartaric acid. In one embodiment of the present invention, the three ingredients of lactic acid, glycolic acid, and tartaric acid may be included in a total amount of at least 2% by weight based on the total composition.

[Additives]

The present invention is a hydrogel composition, which may include water, a polyhydric alcohol, a crosslinking agent, and a hydrophilic polymer are basically mixed when manufacturing a hydrogel. At this time, the hydrophilic polymer is sodium polyacrylate. When hydroxyethyl urea and resacetophenone are used as the main ingredients, sodium polyacrylate provides appropriate gel strength and is also preferable in terms of film-forming ability after hydrogel formation.

In addition, the ingredients and mixing amounts of water or crosslinking agent may be appropriately selected according to ordinary skill in the art and are not particularly limited.

Meanwhile, according to one embodiment of the present invention, in addition to hydroxyethyl urea and resacetophenone as main ingredients, three AHA ingredients may be further included. When three AHA ingredients are further mixed as main ingredients, skin irritation may occur and pH stability may be problematic, but this may be resolved by mixing an appropriate neutralizing agent. The preferred pH range of the composition in the present invention is 4.5 to 5.5.

One embodiment of the present invention excludes parabens (e.g., methylparaben or propylparaben), which are preservatives commonly used in other hydrogel patches, and 1,2-hexanediol may be used to secure antibacterial stability. For reference, parabens are controversial worldwide as being harmful, and it is known that excessive exposure may cause skin itching or atopic eczema, so there is a movement to exclude them as much as possible. However, in products where an appropriate alternative antibacterial agent has not been developed, parabens are still added in small amounts, but in the present invention, antibacterial inhibition is possible only by adding 1,2-hexanediol, one of polyhydric alcohols, and parabens may be excluded altogether.

[Patch]

The patch according to the present invention may be manufactured by applying a hydrogel composition onto a nonwoven fabric. Specifically, according to one embodiment, the hydrogel may be applied to a backing layer such as a nonwoven fabric with a thickness in the range of 0.5 to 1.5 mm, and then a release layer may be laminated thereon, thereby manufacturing a formulation in the form of a patch.

At this time, as the backing layer such as a nonwoven fabric, a flexible, non-drug-absorbing layer that is commonly used may be used, and for example, a nonwoven fabric, a nonwoven fabric laminated with polyurethane, viscose rayon, polyester, polypropylene, nylon, and the like may be used. As the release layer, a film such as polyethylene terephthalate, cast polypropylene, polyethylene coated with a silicone resin or fluorine resin, polyester, polyvinyl chloride, or the like may be used.

Figure 2:
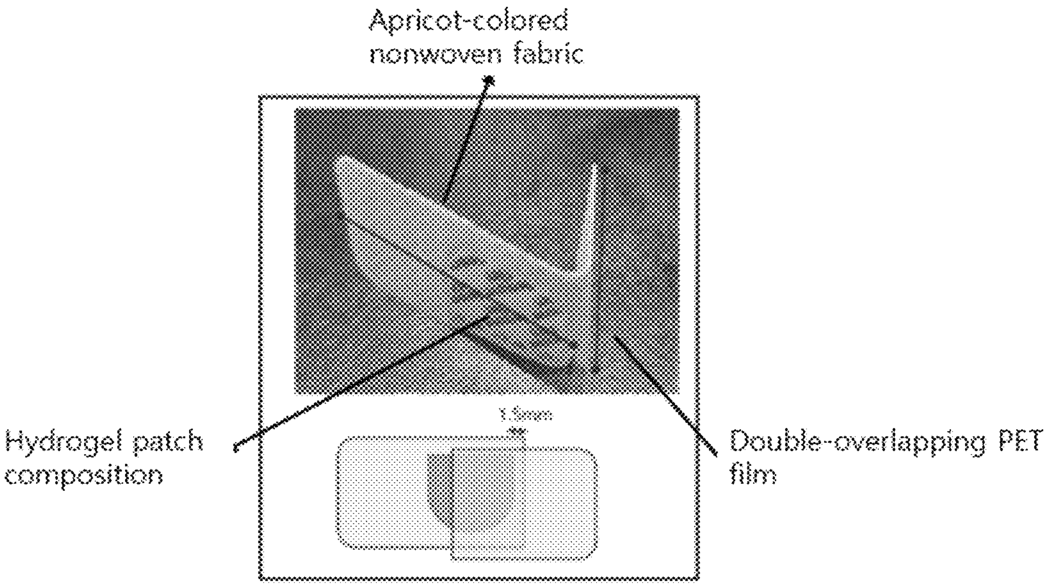

The formulation may be manufactured as a triple structure of a urethane-coated nonwoven fabric (thickness 1 to 2 mm), a matrix hydrogel (thickness 0.5 to 1.5 mm), and a cross-section silicone-treated embossed polyethylene terephthalate (PET) film release paper, as in FIG. 1, or as a triple structure of an apricot-colored nonwoven fabric, a hydrogel patch composition, and a double-overlapping PET film, as shown in FIG. 2, but is not particularly limited.

The patch according to the present invention is characterized in that it is stably attached to the toenail for 8 to 12 hours after attachment, so that the main ingredients may be gradually released.

The following examples supplement the description of the present invention. However, it is to be understood that the scope of the present invention is not limited to the following examples.

EXAMPLE

Hydroxyethyl urea in Table 1 below was prepared as an aqueous solution, and resacetophenone was dissolved in butylene glycol. The remaining ingredients were separately dissolved or dispersed in glycerin or purified water. Finally, all of the dissolved or mixed ingredients were mixed at once, and the resulting mixture was stirred to manufacture a hydrogel.

The contents in Table 1 represent the percentage by weight of each ingredient contained in the hydrogel. Aloe vera extract, lactic acid, glycolic acid, hydroxyethyl urea, disodium ethylenediaminetetraacetic acid (EDTA), and tartaric acid were added to water (approximately 35% to 45% of the total used amount), and the resulting mixture was stirred to prepare an aqueous solution. 1,2-hexanediol, polysorbate 80, tocopheryl acetate, cellulose gum, sodium polyacrylate, and aluminum glycinate were added to glycerin (approximately 25 to 35% of the total amount used) and stirred to prepare a mixed solution. Resacetophenone was added to butylene glycol, and the resulting mixture was stirred to prepare a solution. The final mixing was done by adding and mixing all of the prepared solutions at once to manufacture a hydrogel.

| | Formulation Example 1 | Formulation Example 2 | Formulation Example 3 |
|---|---|---|---|
| Hydroxyethyl urea | 15.00 | 15.00 | — |
| Resacetophenone | 0.50 | — | 0.50 |
| Glycerin | 30.00 | 40.00 | 25.00 |
| Butylene glycol | 7.00 | 7.00 | 7.00 |
| Sodium polyacrylate | 6.00 | 4.00 | 5.50 |
| Cellulose gum | 2.00 | 3.00 | 2.500 |
| Water | 43.52 | 35.02 | 63.52 |
| Aluminum glycinate | 0.12 | 0.12 | 0.12 |
| Disodium EDTA | 0.10 | 0.10 | 0.10 |
| Lactic acid | 1.00 | 1.00 | 1.00 |
| Glycolic acid | 1.00 | 1.00 | 1.00 |
| Tartaric acid | 0.50 | 0.50 | 0.50 |
| Tocopheryl acetate | 0.20 | 0.20 | 0.20 |
| Polysorbate 80 | 0.30 | 0.30 | 0.30 |
| Aloe vera extract | 0.50 | 0.50 | 0.50 |
| 1,2-Hexanediol | 0.30 | 0.30 | 0.30 |
| Total | 100 | 100 | 100 |

Hydrogel patches were manufactured with the compositions according to Formulation Examples 1 to 3, and comparative experiments were conducted as described below.

As a result, Formulation Example 2 showed some appearance-improving effects, but only color improvement was observed, and there was no improvement in dead cell removal.

Formulation Example 3 exhibited dead cell-improving effects, but the appearance-improving effects, such as color improvement, failed to meet the expectations, so the effects were not significantly different from the previous inventions.

On the other hand, Formulation Example 1, which is one embodiment of the present invention prepared by combining the two main ingredients, hydroxyethyl urea and resacetophenone, exhibited improved effects compared to Formulation Examples 2 and 3.

[Experiment 1] Comparison of cuticle improvement effects before and after using the hydrogel patch for toenail of the present invention (the patch manufactured according to Formulation Example 1)

Subjects: 10 adult women

Application method: Attaching the hydrogel patch of the present invention for eight hours every day during bedtime Measurement item: Degree of cuticle improvement (measurement of cuticle area)

Figure 3:
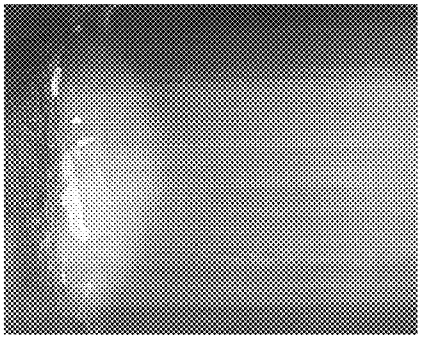
FIG. 3 shows a diagram illustrating the degree of cuticle improvement when a hydrogel patch manufactured according to Formulation Example 1 is attached.
Figure 3:
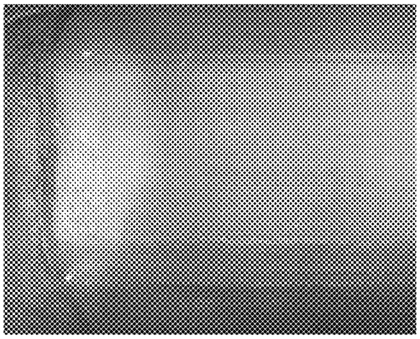
Figure 3:
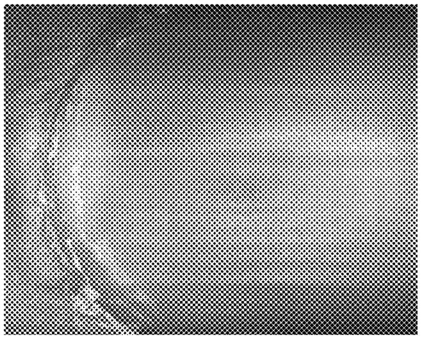
Figure 3:
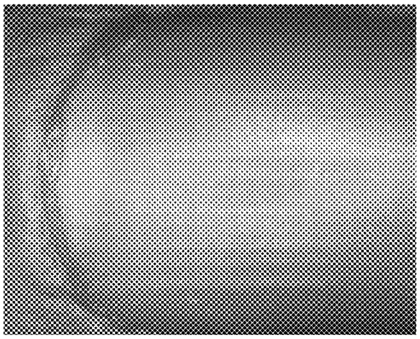

Results: FIG. 3. After using the hydrogel patch of the present invention once, the cuticle was reduced by 26.18%.

[Experiment 2] Comparison of roughness improvement effects before and after using the hydrogel patch for toenail of the present invention Subjects: 10 adult women Application method: Attaching the hydrogel patch of the present invention for eight hours every day during bedtime Measurement items: Degree of roughness improvement (measurement of average roughness)

Figure 4:
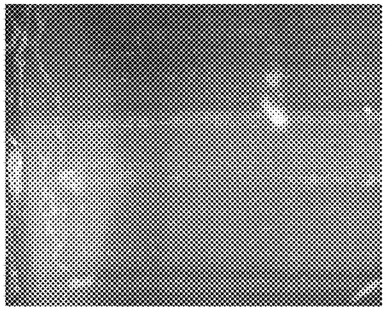
FIG. 4 shows a diagram illustrating the degree of roughness improvement when a hydrogel patch manufactured according to Formulation Example 1 is attached.
Figure 4:
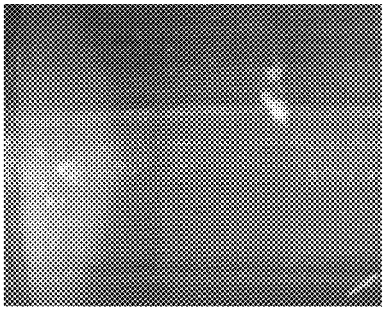
Figure 4:
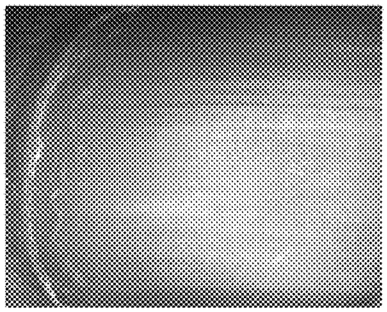
Figure 4:
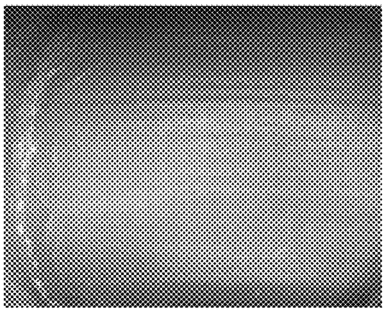

Results: FIG. 4. After using the hydrogel patch of the present invention once, the surface roughness of the application area was reduced by 10.05%.

[Experiment 3] Comparison of hemoglobin concentration before and after using the hydrogel patch for toenail of the present invention Subject: 10 adult women Application method: Attaching the hydrogel patch of the present invention for eight hours every day during bedtime Measurement item: Hemoglobin concentration [Average level (A.U.) measurement]

Figure 5:
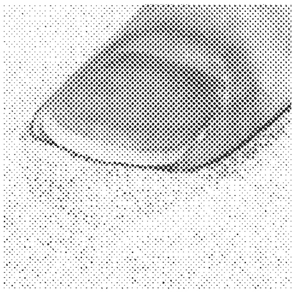
FIG. 5 shows a diagram illustrating the degree of hemoglobin concentration improvement when a hydrogel patch manufactured according to Formulation Example 1 is attached.
Figure 5:
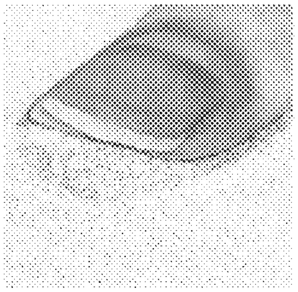
Figure 5:
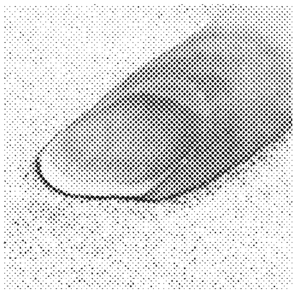
Figure 5:
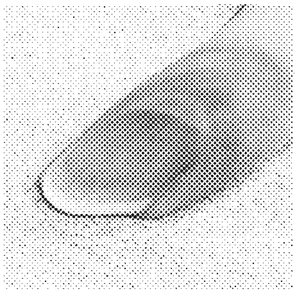

Results: FIG. 5. Immediately after using hydrogel patch of the present invention once, the hemoglobin concentration was improved by 3.28%.

Figure 6:
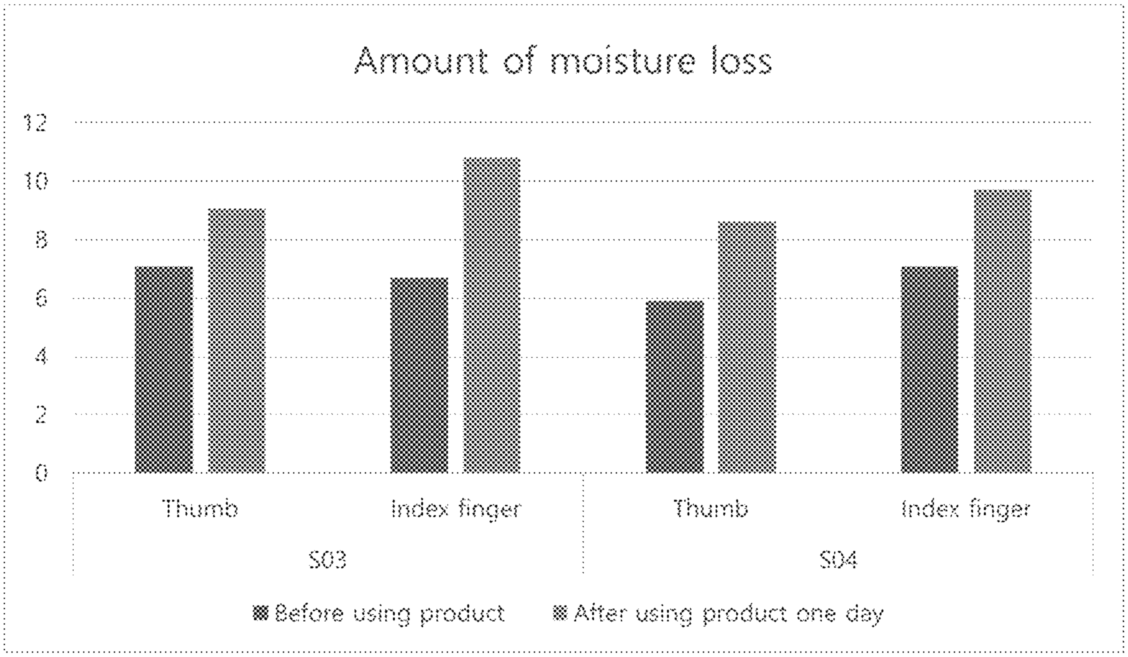
FIG. 6 shows a diagram illustrating the degree of moisture content improvement when a hydrogel patch manufactured according to Formulation Example 1 is attached.

[Experiment 4] Comparison of moisture loss before and after using the hydrogel patch for toenail of the present invention Subject: 10 adult women Application method: Attaching the hydrogel patch of the present invention for eight hours every day during bedtime Measurement item: Moisture loss ($g/m^2$) measurement Results: FIG. 6. The moisture loss increased to 12.01%, but this is a result showing that the moisture content of the nail increased compared to before using the hydrogel patch of the present invention.

What is claimed is:

1. A hydrogel composition for a nail care patch, comprising hydroxyethyl urea and resacetophenone, wherein the hydrogel composition includes sodium polyacrylate as a gel-forming hydrophilic polymer.

2. The hydrogel composition according to claim 1, further comprising lactic acid, glycolic acid, and tartaric acid as nail permeability enhancers of hydroxyethyl urea and resacetophenone.

3. The hydrogel composition according to claim 1, further comprising 1,2-hexanediol without containing parabens.

4. The hydrogel composition according to claim 1, wherein the hydrogel composition is effective for improving cuticles, improving nail surface roughness, or improving hemoglobin concentration in skin around nails.

5. A hydrogel patch manufactured by applying the hydrogel composition according to claim 1 on a nonwoven fabric.

* * * * *